United States Patent
Matousek et al.

(10) Patent No.: US 8,259,902 B2
(45) Date of Patent: Sep. 4, 2012

(54) RAMAN ANALYSIS OF TISSUE AND/OR CALCIFICATIONS

(75) Inventors: Pavel Matousek, Abingdon (GB); Anthony William Parker, Swindon (GB); Nicholas Stone, Gloucester (GB)

(73) Assignee: The Science and Technology Facilities Council, Oxfordshire (GB)

( * ) Notice: Subject to any disclaimer, the term of this patent is extended or adjusted under 35 U.S.C. 154(b) by 0 days.

(21) Appl. No.: 12/225,928

(22) PCT Filed: Apr. 5, 2007

(86) PCT No.: PCT/GB2007/001258
§ 371 (c)(1),
(2), (4) Date: Oct. 2, 2008

(87) PCT Pub. No.: WO2007/113570
PCT Pub. Date: Oct. 11, 2007

(65) Prior Publication Data
US 2009/0238333 A1 Sep. 24, 2009

(30) Foreign Application Priority Data

Apr. 5, 2006 (GB) .................... 0606891.0
Aug. 17, 2006 (GB) .................... 0616376.0

(51) Int. Cl.
*A61B 6/04* (2006.01)
*A61B 6/12* (2006.01)
*G01B 15/00* (2006.01)
*G01J 3/44* (2006.01)

(52) U.S. Cl. .......................... 378/90; 356/301

(58) Field of Classification Search .................... 378/37, 378/70, 86, 87, 88, 90; 356/300, 301
See application file for complete search history.

(56) References Cited

U.S. PATENT DOCUMENTS

| | | | |
|---|---|---|---|
| 3,442,591 A | | 5/1969 | Iwao Ogura et al. |
| 3,770,350 A | * | 11/1973 | Stone et al. .................... 356/301 |
| 4,570,638 A | | 2/1986 | Stoddart et al. |
| 4,645,340 A | | 2/1987 | Graham et al. |
| 4,714,345 A | | 12/1987 | Schrader |
| 4,784,486 A | | 11/1988 | Van Wagenen et al. |
| 4,799,786 A | | 1/1989 | Gerrard |
| 4,945,239 A | * | 7/1990 | Wist et al. .................. 250/358.1 |
| 5,139,025 A | | 8/1992 | Lewis et al. |

(Continued)

FOREIGN PATENT DOCUMENTS

CN 1584555 A 2/2005

(Continued)

OTHER PUBLICATIONS

Brenan et al., Volumetric Raman Microscopy Through a Turbid Medium, Journal of Raman Spectroscopy, vol. 27, (1996), pp. 561-570.

(Continued)

*Primary Examiner* — Anastasia Midkiff
(74) *Attorney, Agent, or Firm* — Birch, Stewart, Kolasch & Birch, LLP

(57) ABSTRACT

Non invasive in-vivo measurement of composition of a tissue within a part of a human or animal subject is carried out by detecting a Raman spectral characteristic in light scattered through the part using a transmission, rather than a backscattering geometry. The technique is applied to the detection of calcifications in human breast tissues.

16 Claims, 8 Drawing Sheets

U.S. PATENT DOCUMENTS

| | | | |
|---|---|---|---|
| 5,194,913 A | 3/1993 | Myrick et al. | |
| 5,261,410 A | 11/1993 | Alfano et al. | |
| 5,349,961 A | 9/1994 | Stoddart et al. | |
| 5,371,368 A | 12/1994 | Alfano et al. | |
| 5,506,678 A | 4/1996 | Carlsen et al. | |
| 5,615,673 A | 4/1997 | Berger et al. | |
| 5,625,458 A | 4/1997 | Alfano et al. | |
| 5,660,181 A | 8/1997 | Ho et al. | |
| 5,752,519 A | 5/1998 | Benaron et al. | |
| 5,873,831 A | 2/1999 | Bernstein et al. | |
| 5,919,140 A * | 7/1999 | Perelman et al. | 600/476 |
| 5,935,062 A | 8/1999 | Messerschmidt et al. | |
| 5,999,836 A | 12/1999 | Nelson et al. | |
| 6,289,230 B1 | 9/2001 | Chaiken et al. | |
| 6,310,686 B1 | 10/2001 | Jiang | |
| 6,654,118 B2 | 11/2003 | Bruce | |
| 6,681,133 B2 | 1/2004 | Chaiken et al. | |
| 6,897,951 B2 | 5/2005 | Womble et al. | |
| 6,919,556 B1 | 7/2005 | Laurence | |
| 7,219,568 B2 | 5/2007 | Folestad et al. | |
| 7,269,245 B2 * | 9/2007 | He et al. | 378/71 |
| 7,697,576 B2 | 4/2010 | Maier et al. | |
| 7,911,604 B2 * | 3/2011 | Matousek et al. | 356/301 |
| 2003/0004419 A1 * | 1/2003 | Treado et al. | 600/476 |
| 2003/0018272 A1 * | 1/2003 | Treado et al. | 600/476 |
| 2003/0085348 A1 | 5/2003 | Megerle | |
| 2003/0120137 A1 | 6/2003 | Pawluczyk | |
| 2003/0220549 A1 | 11/2003 | Liu et al. | |
| 2004/0051867 A1 | 3/2004 | Brestel et al. | |
| 2004/0054270 A1 | 3/2004 | Pewzner et al. | |
| 2004/0063214 A1 | 4/2004 | Berlin et al. | |
| 2004/0092804 A1 * | 5/2004 | Rebec et al. | 600/310 |
| 2004/0263843 A1 | 12/2004 | Knopp et al. | |
| 2005/0010130 A1 | 1/2005 | Morris et al. | |
| 2005/0206892 A1 | 9/2005 | Wang et al. | |
| 2005/0283058 A1 | 12/2005 | Choo-Smith et al. | |
| 2006/0121442 A1 | 6/2006 | Perraut et al. | |
| 2006/0158645 A1 * | 7/2006 | Maier et al. | 356/301 |
| 2006/0249423 A1 | 11/2006 | Reijonen | |
| 2007/0182959 A1 * | 8/2007 | Maier et al. | 356/301 |
| 2008/0051645 A1 * | 2/2008 | Rebec et al. | 600/316 |
| 2009/0177052 A1 * | 7/2009 | Rebec et al. | 600/310 |

FOREIGN PATENT DOCUMENTS

| | | |
|---|---|---|
| EP | 0 781 990 A1 | 7/1997 |
| EP | 1 533 607 A2 | 5/2005 |
| GB | 1171689 | 11/1969 |
| GB | 1510827 | 5/1978 |
| GB | 2244329 A | 11/1991 |
| JP | 56-22938 A | 3/1981 |
| JP | 8-75652 A | 3/1996 |
| JP | 9-127001 A | 5/1997 |
| JP | 2002-85385 A | 3/2002 |
| JP | 2004-271220 A | 9/2004 |
| JP | 2005-70009 A | 3/2005 |
| JP | 2006-214899 | 8/2006 |
| WO | WO-92/15008 A1 | 9/1992 |
| WO | WO 96/06346 A1 | 2/1996 |
| WO | WO-96/26431 A1 | 8/1996 |
| WO | WO 97/22872 A1 | 6/1997 |
| WO | WO-98/00057 A1 | 1/1998 |
| WO | WO 99/32872 A1 | 7/1999 |
| WO | WO 00/07705 A1 | 2/2000 |
| WO | WO 00/16036 A1 | 3/2000 |
| WO | WO 00/20843 A1 | 4/2000 |
| WO | WO 01/22063 A1 | 3/2001 |
| WO | WO 01/39665 A2 | 6/2001 |
| WO | WO-01/52739 A1 | 7/2001 |
| WO | WO 01/57500 A1 | 8/2001 |
| WO | WO 01/60503 A1 | 8/2001 |
| WO | WO-02/07585 A2 | 1/2002 |
| WO | WO 02/061394 A1 | 8/2002 |
| WO | WO 03/023382 A1 | 3/2003 |
| WO | WO 03/041123 A3 | 5/2003 |
| WO | WO-03/073082 A1 | 9/2003 |
| WO | WO-03/087793 A1 | 10/2003 |
| WO | WO 2004/031749 A2 | 4/2004 |
| WO | WO-2004/078044 A1 | 9/2004 |
| WO | WO 2004-294150 A | 10/2004 |
| WO | WO-2004/097365 A2 | 11/2004 |
| WO | WO 2004/102186 A1 | 11/2004 |
| WO | WO 2004/111639 A1 | 12/2004 |
| WO | WO-2005/004714 A1 | 1/2005 |
| WO | WO 2005/060622 A2 | 7/2005 |
| WO | WO-2006/061565 A1 | 6/2006 |
| WO | WO-2006/061566 A1 | 6/2006 |
| WO | WO 2006/083316 A2 | 8/2006 |
| WO | WO 2006/091223 A2 | 8/2006 |
| WO | WO-2007/040589 A1 | 4/2007 |
| WO | WO 2008/024288 A2 | 2/2008 |

OTHER PUBLICATIONS

Matousek et al., Subsurface probing in diffusely scattering media using spatially offset Raman spectroscopy Applied Spectroscopy, vol. 59, No. 4, Apr. 2005, pp. 393-400.

Matousek et, al. Efficient Rejection of Fluorescene from Raman Spectra Using Picosecond Kerr Gating, vol. 53, No. 12, 1999, pp. 1485-1489.

Haka et al., Identifying Microcalification in Benign and Malignant Breast Lesions by Probing Differences in Their Chemical Composition Using Raman Spectroscopy, Cancer Research, vol. 62, Sep. 15, 2002, pp. 5375-5380.

Sun et al., Basic calcium phosphate crystals stimulate the endocytotic activity of cells-inhibition by anti-calcification agents, BBRC, vol. 312, (2003), pp. 1053-1059.

Haka et al., Diagnosing breast cancer by using Raman spectroscopy, PNAS, vol. 102, No. 35, Aug. 30, 2005, pp. 12371-12376.

Weng et al., FTIR fiber optics and FT-Raman spectroscopic studies for the diagnosis of cancer, American Clinical Laboratory, vol. 19, Aug. 2000, p. 20.

Dukor et al., A new, Non-Destructive Method for Analysis of Clinical Samples with FT-IR Microspectroscopy., Breast Cancer Tissue as an example, Cellular and Molecular Biology, vol. 44, No. 1, (1998), pp. 211-217.

Myrick et al., Comparison of some fiber optic configurations for measurement of luminescence and Raman scattering, Applied Optics, vol. 29, No. 9, Mar. 20, 1990, pp. 1333-1344.

Matousek et al., Fluroescence suppression in resonance Raman spectroscopy using a high-performance picosecond Kerr gate, Journal of Raman Spectroscopy, vol. 32, 2001, pp. 983-988.

Matousek et al., Depth Profiling in Diffusely Scattering Media Using Raman Spectroscopy and Picosecond Kerr Gating, Applied Spectroscopy, vol. 59, No. 2, 2005, pp. 200-205.

Everall et al., Picosecond Time-Resolved Raman Spectroscopy of Solids: Capabilities and Limitations for Fluorescence Rejection and the Influence of Diffuse Reflectance, Applied Spectroscopy, vol. 55, No. 12, 2001, pp. 1701-1708.

Everall et al., Photon Migration in Raman Spectroscopy, Applied Spectroscopy, vol. 58, No. 5, 2004, pp. 591-597.

Morris et al., Kerr-gated time-resolved Raman spectroscopy of equine cortical bone tissue, Journal of Biomedical Optics, vol. 10, No. 1, (Jan./Feb. 2005), pp. 014014-1-01401-7.

Draper et al., Novel Assessment of Bone Using Time-Resolved Transcutaneous Raman Spectroscopy, Journal of Bone and Mineral Research, vol. 20, No. 11, 2005, pp. 1968-1972.

Schulmerich et al., Subsurface Raman Spectroscopy and Mapping Using a Globally Illuminated Non-Confocal Fiber-Optic Array Probe in the Presence of Raman Photon Migration, Applied Spectroscopy, vol. 60, No. 2, 2006, pp. 109-114.

Schulmerich et al., Transcutaneous Raman spectroscopy of bone tissue using a non-confocal confocal fiber optic array probe, Proc. of SPIE, vol. 6093, pp. 609300-1, 609300-7.

Hanlon et al., Prospects for in vivo Raman spectroscopy, Phys. Med. Bio., vol. 45, pp. R1- R59.

Peltier et al., Raman microspectroscopic model of human breast tissue: implications for breast cancer diagnosis in vivo, Journal of Raman Spectroscopy, vol. 33, 2002, pp. 552-563.

Schrader et al., Laser-based molecular spectroscopy for chemical analysis Raman scattering processes, Pure & Appl. Chem., vol. 69, No. 7, 1997, pp. 1451-1468.

Stone et al., Near-infrared Raman spectroscopy for the classification of epithelial pre-cancers and cancers, Journal of Raman Specteoscopy, vol. 33, 2002, pp. 564-573.

Kincade, Optical diagnostics image tissues and tumors, Laser Focus World, vol. 32, No. 2, Feb. 1996, 5 page printout.

Hasegawa, Detection of minute chemical signals by principal component analysis, Trends in Analytical Chemistry, vol. 20, No. 2, 2001, pp. 53-64.

Wu et al., Three dimensional imaging of objects embedded in turbid media with fluorescence and Raman spectroscopy, Applied Optics, vol. 34, No. 18, Jun. 20, 1995, pp. 3425-3430.

Ma et al., Rapid Micro-Raman Imaging using Fiber-Bundle Image Compression, Applied Spectroscopy, vol. 51, No. 12, 1997, pp. 1845-1848.

Dunsby et al., Techniques for depth-resolved imaging through turbid media including coherence-gated imaging, Journal of Physics D. Applied Physics, vol. 36, (2003), pp. R207-R227.

Matousek, et al., "Numerical Simulations of Subsurface Probing in Diffusely Scattering Media Using Spatially Offset Raman Spectroscopy", Applied Spectroscopy, vol. 59, No. 12, pp. 1485-1492, May 3, 2005.

Bell et al., Composition profiling of seized ecstasy tablets by Raman spectroscopy, Analyst, vol. 125, 2000, pp. 1811-1815.

Breitenbach et al., Pharmaceutical Research, Confocal Raman-Spectroscopy: Analytical Approach to Solid Dispersions and Mapping of Drugs, vol. 16, No. 7, 1999, pp. 1109-1113.

Butterfield, Through-package applications of Raman spectroscopy for nondestructive identification of product, American Laboratory News, Nov. 1999, p. 14.

Carter, et al., Raman spectroscopy for the in situ identification of cocaine and selected adulterants, Applied Spectroscopy, The Society for Applied Spectroscopy, Baltimore, US vol. 54, No. 12, Dec. 2000, pp. 1876-1881.

Coates, Molecular spectroscopy workbench new technologies for process analytical and quality control applications: Compact Raman, Spectroscopy, Advanstar Communications, US, vol. 21, No. 2, Feb. 2006, pp. 68-74.

Das et al., Time-resolved fluorescence and photon migration studies in biomedical and model random media, Rep. Prog Phys., vol. 60, pp. 227-292 (1997).

Dyrby et al., Chemometric Quantitation of the Active Substance (Containing C$\equiv$N) in a Pharmaceutical Tablet Using Near-Infrared (NIR) Transmittance and NIR FT-Raman Spectra, vol. 56, No. 5, 2002, pp. 579-585.

Eliasson et al., Non-invasive detection of cocaine dissolved in beverages using displaced Raman spectroscopy, Analytica Chimica Acta, Elsevier, Amsterdam NL, vol. 607, No. 1, Nov. 19, 2007, pp. 50-53.

Eliasson et al., Non-invasive detection of concealed liquid explosives using Raman spectroscopy, Analytical Chemistry Nov. 1, 2007, vol. 79, No. 21, pp. 8185-8189.

Hausman et al., Application of on-line Raman spectroscopy for characterizing relationships between drug hydration state and tablet physical stability, International Journal of Pharmaceutics, vol. 299, (2005), pp. 19-33.

Johansson et al., Characterization of different laser irradiation methods for quantitative raman tablet assessment, Journal of Pharmaceutical and Biomedical Analysis, vol. 39, (2005), pp. 510-516.

Lewis et al., Raman spectroscopic studies of explosive materials: towards a fieldable explosives detector, Spectrochimica Acta, Part A (Molecular Spectroscopy) Elsevier UK, vol. 51A, No. 12, Nov. 16, 1995, pp. 1985-2000.

Matousek et al., Bulk Raman Analysis of Pharmaceutical Tablets, Applied Spectroscopy, vol. 60, No. 12, 2006, pp. 1353-1357.

Matousek et al., Fluorescence background suppression in Raman spectroscopy using combined Kerr gated and shifted excitation Raman difference techniques, Journal of Raman Spectroscopy, vol. 33, No. 4, Apr. 2002, pp. 238-242.

Matousek et al., Non-invasive probing of pharmaceutical capsules using transmission Raman spectroscopy, Journal of Raman Spectroscopy, vol. 38, 2007, pp. 563-567.

Matousek et al., Noninvasive Raman Spectroscopy of human tissue in vivo, Applied Spectroscopy, The Society for Applied Spectroscopy, Baltimore, US, vol. 60, No. 7, Jul. 2006, pp. 758-763.

Matousek et al., Prospects for the diagnosis of breast cancer by noninvase probing of calcifications using transmission Raman spectroscopy, Journal of Biomedical Optics, vol. 12, No. 2, Mar./Apr. 2007, pp. 024008-1-024008-8.

Matousek, Deep non-invasive Raman spectroscopy of living tissue and powders, Chemical Society Review, vol. 36, 2007, pp. 1292-1304.

Matousek, Inverse spatially offset raman spectroscopy for deep noninvasive probing of turbid media, Applied Spectroscopy, The Society for Applied Spectroscopy, Baltimore, US, vol. 60 No. 11, Nov. 1, 2006, pp. 1341-1347.

Matousek, Raman Signal Enhancement in Deep Spectroscopy of Turbid Media, Applied Spectroscopy, vol. 61, No. 8, 2007, pp. 845-854.

Niemczyk, et al., Quantitative Determination of Bucindolol Concentration in Intact Gel Capsules Using Raman Spectroscopy, Department of Chemistry, University of New Mexico, Albuquerque, New Mexico 87131, pp. 2762-2765.

Schrader et al., "Die Intensität des Ramanspektrums polykristalliner Substanzen," Fresenius Journal of Analytical Chemistry, vol. 225, 1967, pp. 230-247.

Schrader et al., Bulk raman Analysis of Turbid Media, Applied Spectroscopy, vol. 60, (2006), pp. 230-246.

Schulmerich et al., Transcutaneous fiber optic Raman spectroscopy of bone using annular illumination and a circular array of collection fibers, Journal of Biomedical Optics, vol. 11, No. 6, Nov./Dec. 2006.

Sun et al., Basic calcium phosphate crystals stimulate the endocytotic activity of cells-inhibition by anti-calcification agents, Biochemical and Biophysical Research Communications, vol. 312, pp. 1053-1059, (2003).

Szostak et al., Quantitative determination of acetylsalicylic acid and acetaminophen in tablets by FT-Raman spectroscopy, Analyst, vol. 127, 2002, pp. 144-148.

Taylor et al., Journal of Pharmaceutical, Evaluation of Solid-State Forms Present in Tablets by Raman Spectroscopy, vol. 89, No. 10, Oct. 2000, pp. 1342-1353.

Wang et al., Direct assay and shelf-life monitoring of aspirin tablets using Raman spectroscopy, Journal of Pharmaceutical and Biomedical Analysis, vol. 16, (1997), pp. 87-94.

Williams et al., Evaluation of drug physical form during granulation, tabletting and storage, International Journal of Pharmaceutics, vol. 275, (2004), pp. 29-39.

B. Schrader and G. Bergmann, "Die Intensität des Ramanspektrums polykristalliner Substanzen", Fresenius Journal of Analytical Chemistry, vol. 225, p. 230-247, 1967.

J. Klosowski and E. Steger, "Experiments on Raman Versus Primary Light Scattering Fluxes From Pressed Discs", Journal of Raman Spectroscopy, vol. 8, No. 3, p. 169-171, 1979.

* cited by examiner

RAMAN ANALYSIS OF TISSUE AND/OR CALCIFICATIONS

FIELD OF THE INVENTION

The present invention relates to methods and apparatus for measurement of composition of a tissue within a human or animal subject, and in particular to such measurement made non invasively in vivo. By way of example only, the invention may be applied to the measurement of microcalcifications in tissue within a human breast, or to the measurement of bone, cartilage or other tissue composition in a finger, toe, hand or foot.

INTRODUCTION

Raman spectroscopy is the study of small shifts in the wavelength of photons, usually generated by a laser, as the photons undergo inelastic Raman scattering with molecules in various media. Interaction with different molecules gives rise to different spectral shifts, so that analysis of a Raman spectrum can be used to determine chemical composition of a sample. The very weak nature of the scattering makes Raman spectroscopy difficult to use in many circumstances, due to the Raman signal being swamped by fluorescence and other background signals.

DISCUSSION OF THE PRIOR ART

Raman spectroscopy has been used to analyse a wide variety of biological tissues. For example, Haka et al. "Identifying Microcalcifications in Benign and Malignant Breast Lesions by Probing Differences in Their Chemical Composition Using Raman Spectroscopy", Cancer Research 62, 2002 discusses the use of Raman spectroscopy to analyse the chemical composition of microcalcifications occurring in benign and malignant lesions in tissue samples removed from human breasts.

The use of Raman spectroscopy to determine aspects of tissue composition in vivo has also been proposed, for example in Hanlon et al. "Prospects for in vivo Raman spectroscopy" Phys. Med. Biol. 45,2000, and is also proposed for the purposes of human breast cancer diagnosis in Shafer-Peltier et al. "Raman microscopic model of human breast tissue: implications for breast cancer diagnosis in vivo", J. Raman. Spectroscopy 33, 2002. This document discusses using a fibre optic needle device which is inserted into a breast and manoeuvred to the location of a lesion, in particular to study the composition of calcifications.

Breast calcifications can be found in both benign and malignant lesions and the chemical composition of these can indicate possible diseased state. Calcium oxalate (dihydrate) (COD) is associated with benign lesions, however calcium hydroxyapatite (HAP) is found mainly in malignant tissue. As current practices such as mammography and histopathology examine the morphology of the specimen, they can not reliably distinguish between the two types of calcifications. Shadows in mammograms are often the only features that indicate the presence of a cancerous lesion.

US2005/0010130A1 discusses the use of Raman and other spectroscopic techniques to determine aspects of bone composition, either in vivo through the skin or via an incision, of by taking a biopsy. WO03/073082A1 discloses the use of confocal Raman spectroscopy to make depth selective measurements of pH within skin.

FIG. 1 illustrates a scheme using Raman spectroscopy to detect, in vivo, characteristics of human or animal tissue, which is similar to that proposed in WO03/073082. A laser source 10 provides photons to confocal optics 12 which directs the photons into the surface tissue of a subject. Raman scattering events 16 change the frequency of some of the photons, and some of the Raman scattered photons are backscattered to be collected by the confocal optics 12 and directed to a spectral analyser 18. An output of the spectral analyser is interpreted by a computer 20 to infer characteristics of the tissue within which the Raman scattering took place.

A scheme such as that illustrated in FIG. 1 can be used to determined properties of tissue at or very close to the surface, for example, in the top few tens of micrometers. Although Raman scattering occurs deeper within the sample, the intensity of the incident radiation, and the number of Raman scattered photons backscattered to the sample surface drops off rapidly with depth, and quickly becomes swamped by fluorescence and other background signals. To overcome this problem, and probe deeper within the sample, the collected photons can be time gated to exclude the time delayed fluorescence signal, as described in Morris et al. "Kerr-gated time-resolved Raman spectroscopy of equine cortical bone tissue", J. Biomedical Optics 10 2005, in which a Raman signal from about 300 micrometers below the surface was detected. However, the apparatus to achieve such time gating is complex, and the increased depth of detection is rather minimal compared with typical thicknesses of skin and other soft tissue through which it would be desirable to probe in human and animal subjects.

OBJECTS OF THE INVENTION

It is an object of the invention to provide improved methods and apparatus for measurement, and especially non invasive in vivo measurement, of the composition of tissue within the human or animal body.

It is also an object of the invention to provide methods and apparatus which use Raman spectroscopy to probe to increased depths within human or animal tissue.

It is also an object of the invention to provide methods and apparatus for non-invasive in-vivo measurement of the composition of calcified tissue with a part of a human or animal body, especially within a breast.

The present invention addresses these and other problems of the related prior art.

SUMMARY OF THE INVENTION

The invention provides a method of probing within a part of a human or animal subject by directing probe light at a first surface of the part, and collecting scattered light from a second, opposing side of the part. Raman spectral features within the collected light are measured and used to determine characteristics of tissue within the part, such as the presence of particular substances. The invention is particularly advantageous because it allows non-invasive in vivo probing of parts of the human or animal body, and unlike prior art Raman techniques which are very heavily biased towards a thin surface layer, characteristics of an internal bulk of the part between the first and second sides are probed.

Using the method, light which has been forward scattered through the body part in a transmission geometry, rather than being backscattered in a more conventional reflection geometry, is collected and analysed.

The invention also provides corresponding apparatus, for example comprising illumination optics and collection optics arranged or directed at first and second opposing sides of a body part, a light source providing probe light to the illumination source, and a spectral analyser adapted to receive collected light from the collection optics and to determine one or more Raman spectral characteristics of the collected light. The spectral analyser could be provided, for example, by selected filters and suitable photon detection apparatus, or a conventional or fourier transform spectrograph.

The invention also provides methods and apparatus for directing probe light at a first surface of a human or animal subject, collecting light at a second surface of the subject, and detecting a Raman spectral signal deriving from Raman scattering within an intervening tissue.

In particular, the invention provides a method of non invasive in vivo measurement of composition of a tissue within a part of a human or animal subject, comprising: directing radiation into the part through a first exterior surface region of the part; collecting a portion of said radiation emerging at a second exterior surface region of the part following forward scattering through the part;

detecting, in said collected radiation, characteristics of said radiation arising from Raman scattering by said tissue; and determining a measurement of composition of said tissue from said characteristics.

Preferably, the second surface region is spaced from said first surface region, preferably by an intervening volume of the tissue. Preferably, at least some of said tissue is disposed between, and more preferably directly between the first and second surfaces. In particular, the second surface region may be on an opposite side of the part from the first surface region, at least during the steps of directing and collecting.

The measurement of composition may be a measurement of composition of calcifications within said tissue, for example a measurement of at least one of a type I, calcium oxalate material and a type II, calcium phosphate material, for example calcium hydroxyapatite material. Such measurements are particularly suitable if the body part is a human or animal breast, in which case the breast may be compressed between opposing clamp or plate surfaces such that the first and second exterior surfaces of the breast are compressed towards each other by the clamp surfaces.

The invention also provides a method of diagnosing a disease, such as a breast cancer condition, comprising determining said measurement of composition as set out above, and making a diagnosis of the disease based on said measurement of composition.

The invention may be carried out on a variety of body parts such as a digit, limb, lip, ear, eyelid, tooth, tongue or nose, and the tissue may comprise one or more of tissues such as bone, cartilage, bone marrow, brain, nerves, lipids, blood, teeth and breast tissue.

BRIEF DESCRIPTION OF THE DRAWINGS

Embodiments of the invention will now be described, by way of example only, with reference to the accompanying drawings of which.

DETAILED DESCRIPTION OF EMBODIMENTS

Figure 1:
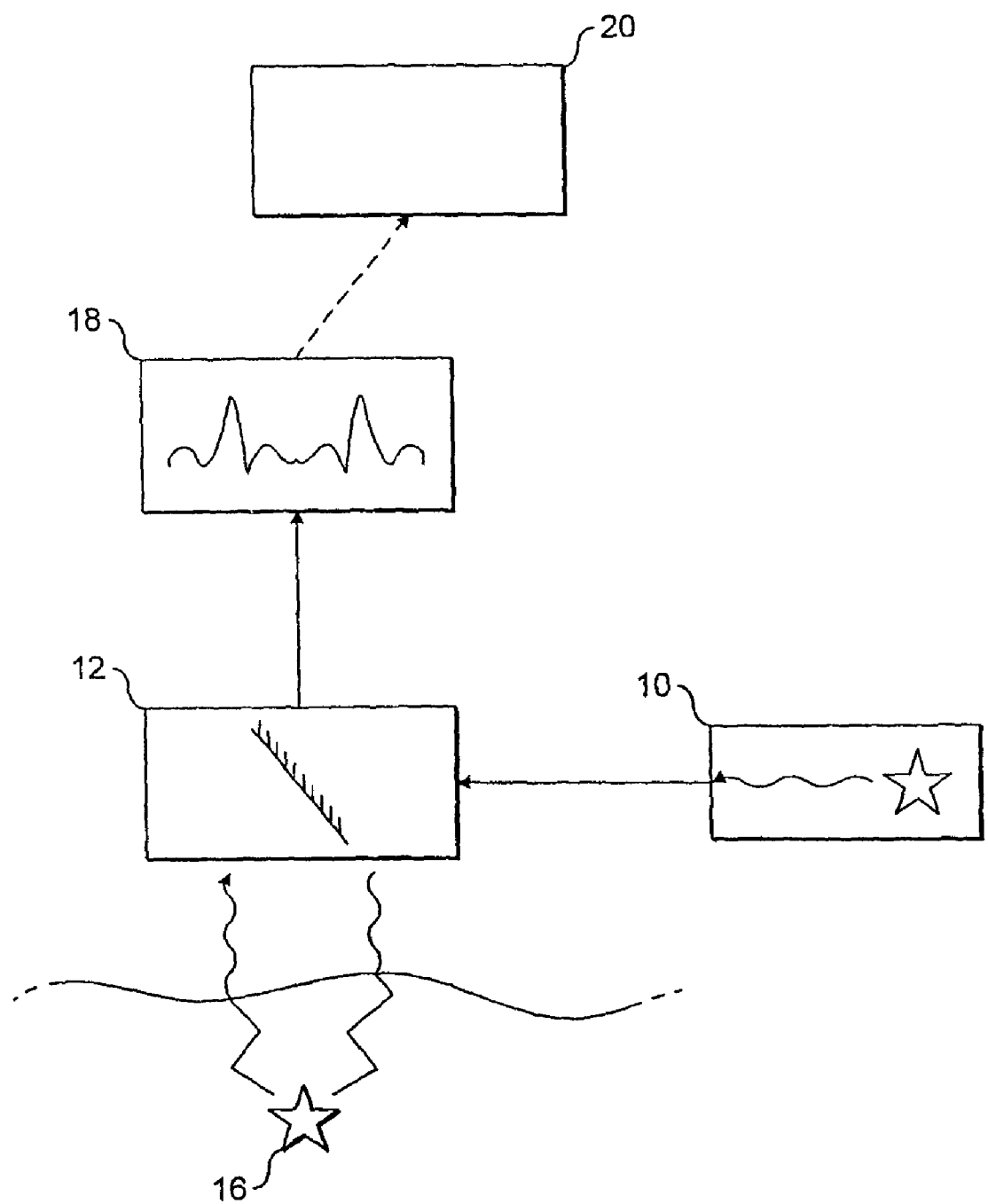
FIG. 1 illustrates Raman probing of tissue using a backscattering geometry.
Figure 2:
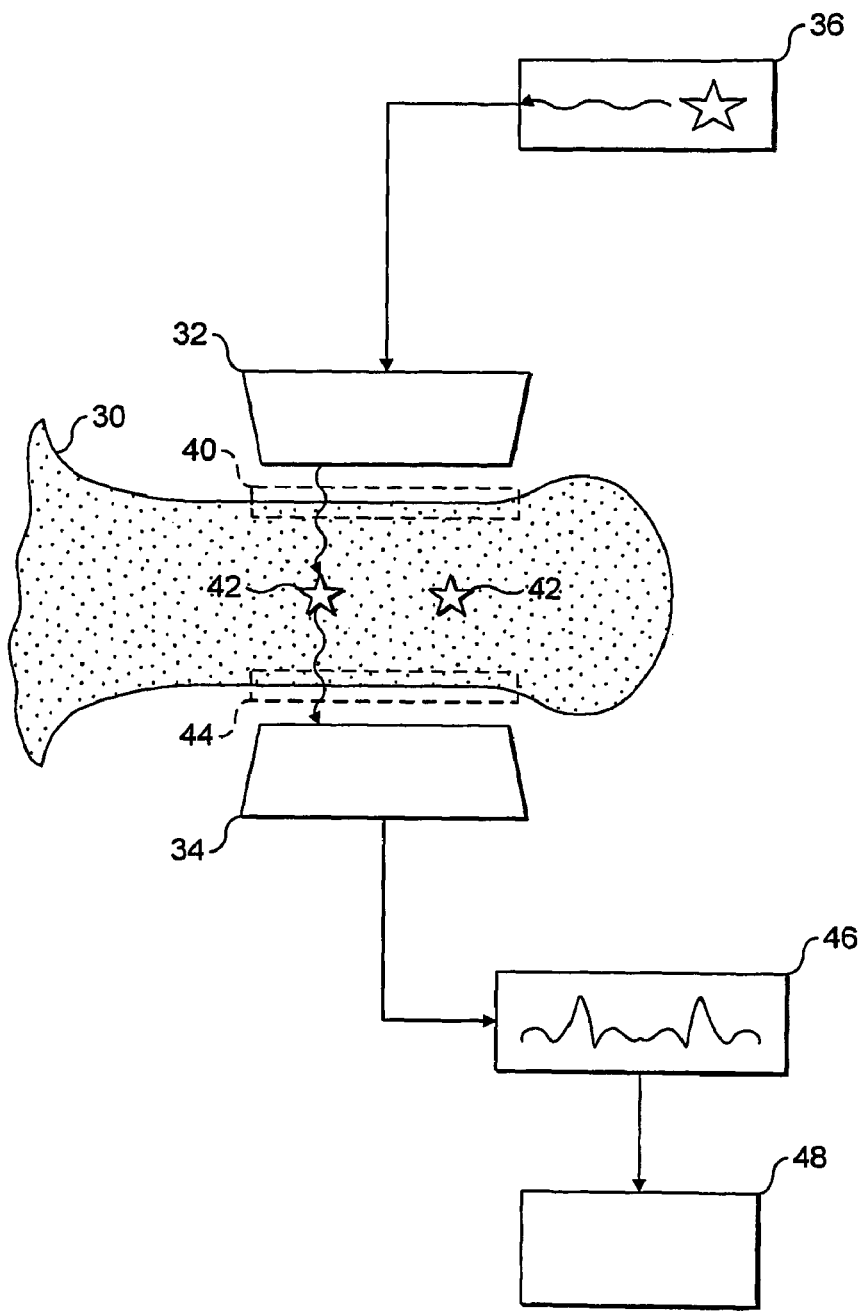
FIG. 2 illustrates Raman probing of a body part using a forward scattering, transmission geometry.

Referring now to FIG. 2, a part 30 of a human or animal body is shown in cross section disposed between illumination optics 32 and collection optics 34. A laser 36 provides a source of photons to the illumination optics 32, which directs the photons into the body part through a first external surface region 40 of the part. Inside the part, a small proportion of the photons undergo Raman scattering events 42 and are shifted in frequency by an amount dependent upon the tissue, and in particular the molecule within the tissue at which the scattering event takes place. Some of the Raman scattered photons pass out of the body part 30 through a second external surface region 44 of the part and are collected by the collection optics 34.

The illumination optics and collection optics are disposed around the body part such that the collected photons have been forward scattered through the body part in a transmission geometry, rather than having been backscattered in a reflection geometry. In particular, the illumination and collection optics may be disposed on opposite sides of the body part when the method is carried out, preferably such that the tissue to be measured lies between the first and second surface regions.

The photons collected by the collection optics are suitably analysed to determine characteristics of the Raman scattering taking place in the tissue. In the arrangement of FIG. 2 a spectral analyser 46, which could for example be a fourier transform spectrograph, or use one or more narrow pass filters, detects characteristics of the Raman photons. A computer 48 processes the data provided by the spectral analyser, for example to provide an indication of the chemical characteristics or composition of the tissue.

In practise, the illumination and collection optics could take a variety of forms, such as bundles of optical fibres which can be manipulated for appropriate positioning adjacent to the first and second surface areas. The illumination and collection optics may be provided with automated means for scanning across the surfaces of the sample, and/or may be provided with distinct segments which can be selectively used to illuminate and/or collect photons from different parts of the part.

The body part can be any of a variety of different body parts, and the illumination and collection optics may be adapted accordingly. For example, the body part may be a digit or limb such as a finger, toe, foot, hand or ear, and the tissue measured could be bone, cartilage, joint fluid, blood or skin.

Figure 3:
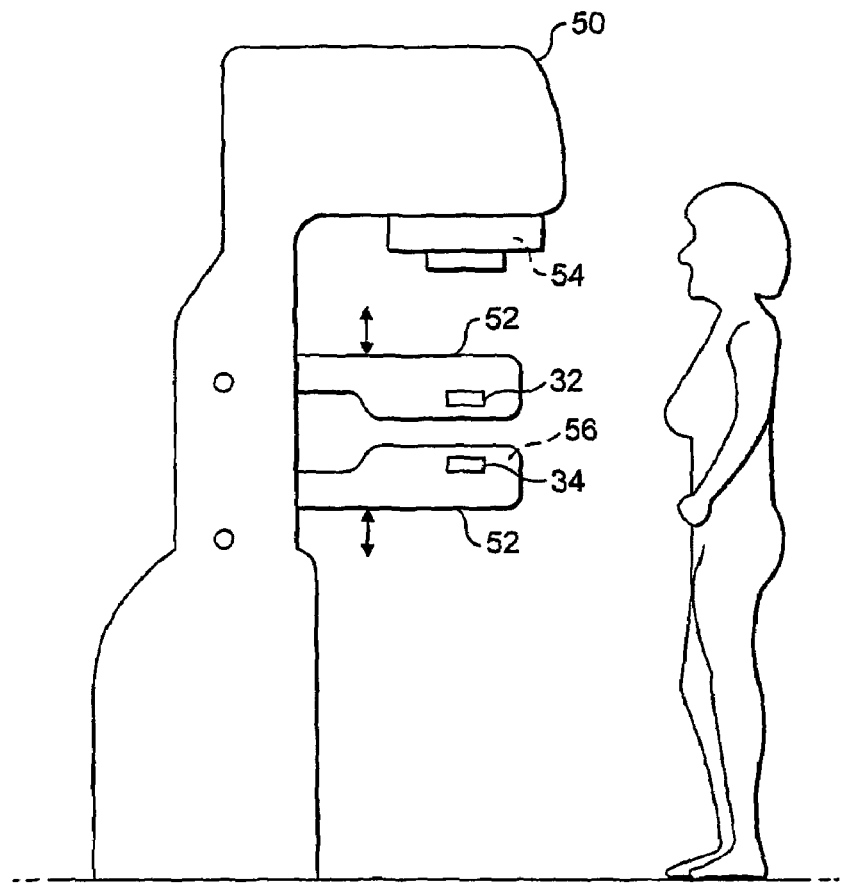
FIG. 3 shows a machine adapted for Raman probing of breast tissue in a clinical environment.

Mounts or other constraining or positioning means may be provided in order to present the body part to the optics. FIG. 3 illustrates a machine 50 for carrying out the invention on human breasts. The machine is similar in many respects to X-ray machines familiar in the prior art for obtaining mammographic images used to detect breast cancer. In use, a human breast is placed between two breast clamps or plates 52, typically made of or at least faced with a transparent plastic, which are then adjusted to compress the bulk of the breast to a thickness of about 2 cm. In prior art machines an X-ray source 54 is housed above the breast clamps 52, and an X-ray camera 56 or film is housed in the lower breast clamp. In the embodiment of FIG. 3, however, one of the breast clamps incorporates the illumination optics 32 of FIG. 2, and the other breast clamp incorporates the collection optics 34. The optics may be automatically driven to scan across the clamped breast, may be automatically driven or manually adjustable to be directed at a particular region of interest, or they may be of sufficient extent to cover a substantial portion of the clamped breast. Furthermore, the machine 50 may either include or not include X-ray facilities as described above. If X-ray facilities are included then X-ray image data may be used to direct operation of the Raman optics to study a particular part of a breast.

Although not illustrated in FIG. 3, the machine 50 preferably also includes means for spectral analysis of the collected Raman light, and computer apparatus for processing the results of the spectral analysis to present useful information to a clinician. For example, the computer apparatus could be implemented to interpret the results of the spectral analysis in order to output data indicating the degree of presence of different chemical types of calcification in the probed breast tissue.

The methods and apparatus described above may in particular be used to detect and measure calcifications in breast and other tissues, for example by distinguishing between the different types of calcifications found in breast tissue which are discussed below. Calcifications are found in may different biological tissues, forming both as natural products, e.g. in bones and teeth, and in soft tissues as a result of disease. Natural calcifications are present as a mineralization product in bone, and consist of the specific mineral hydroxyapatite. Pathological calcifications are associated with many medical conditions such as diabetes, breast cancer and crystals-associated osteoarthritis. The deposition of calcium crystals on cells induces detrimental cellular effects and speeds up the progression of the associated diseases.

The presence of calcifications in mammographic images is a feature of particular diagnostic significance, as sometimes this may be the only marker of a malignant breast lesion. Mammography can detect small masses, areas of distortion, ill-defined densities and microcalcifications not detectable by physical examination. However, as this relies only on the morphology of the specimen, it has no definitive criteria for classifying benign and malignant calcifications. It has in fact been found that only 10-25% of mammographically detected lesions are found to be malignant upon needle biopsy.

Microcalcifications can be divided into two types; type I, which consist of calcium oxalate dehydrate (COM), and type II deposits, which are composed of calcium phosphates, mainly calcium hydroxyapatite (HAP). At present, there is no reliable way to distinguish between these two types of calcification by mammography, but the type is thought to correlate with disease (for example, see Haka A. S. et al., "Identifying differences in microcalcifications in benign and malignant breast lesions by probing differences in their chemical composition using Raman spectroscopy", Cancer Research 62 (2002) 5375-5380). Calcium oxalate crystals are mainly found in benign ductal cysts and rarely found in carcinoma, whereas calcium hydroxyapatite deposits are often found in carcinoma.

The methods and apparatus described herein may be used to measure the chemical make-up of lesions and calcifications non-invasively and in vivo, permitting a more simplistic decision for diagnosing breast lesions. This can be used to reduce patient trauma, time delay, and high medical costs associated with the biopsy of benign lesions.

Numerical Model

A Monte Carlo model was used to simulate the transport of illumination photons and Raman photons scattering within a turbid medium such as the body part 30 of FIG. 2. The model was used to calculate the relative intensities of backscattered and forward scattered Raman photons as a function of their depth within the turbid medium. Briefly, both the elastically (illumination) and non-elastically (Raman) scattered photons were individually followed as they propagated through the medium in random walk-like fashion in three-dimensional space. A simplified assumption was made that in each step a photon propagated in a straight line over a distance t and thereafter its direction was fully randomised at the next scattering event. Although this picture is simplistic from the standpoint of individual scattering events, photons propagating through a turbid medium typically have to undergo a number of scattering events (e.g. 10-20) before their original direction of propagation becomes fully scrambled. This is due to the fact that individual scattering events are often strongly biased towards the forward direction. However, it has been shown that for large propagation distances such as those pertinent to the study of subsurface tissues, as of interest here, the individual multiple scattering events can be approximated as a single composite event occurring over the 'randomisation length' t (Matousek P. et al., Applied Spectroscopy 59, p1485, 2005). This simplified assumption enables analysis of large propagation distances with modest computational expense.

The propagation distance, t, over which the photon direction is randomised, can be crudely approximated as the transport length of the scattering medium (lt) (Brenan C. and Hunter I., Journal of Raman Spectroscopy 27, p561, 1996) which is defined in a similar manner as the average distance photons must travel within the sample before deviating significantly from their original direction of propagation. The transport length is typically an order of magnitude longer than the mean free scattering length (ls) of photons in the medium; the precise relation is $ls=(1-g)lt$, where g is the anisotropy for the individual scattering event. In the present model it was also assumed that the wavelength of light propagating through the medium was substantially shorter than the scattering length ls.

Figure 4:
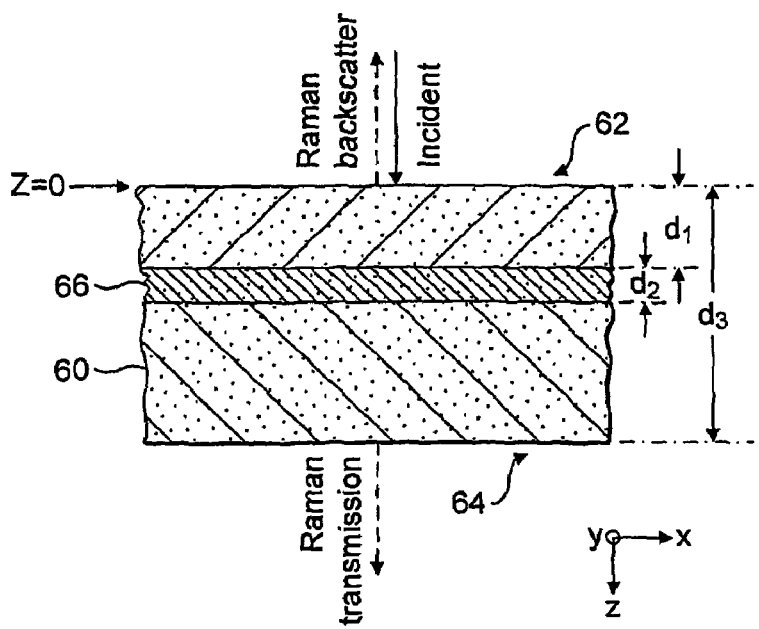
FIG. 4 shows the structure of a sample idealised body part used in a Monte Carlo scattering model.

The modelled sample body part 60 is illustrated in FIG. 4. The sample body part was considered to extend to infinity in x and y directions, with an air-medium interface located at the top surface 62 $z=0$ and bottom surface 64 $z=d3$, where z is a Cartesian coordinate normal to the interface plane. The sample body part was modelled as a uniform turbid medium apart from an intermediate-layer 66 having a different Raman signature to represent a tissue of interest, the intermediate layer having a thickness d2 with a top surface located at depth d1. The overall modelled sample thickness was d3 ($d3>=d1+d2$). That is, the bulk sample medium was located at depths z1 such that $d1>z1>0$ and $d3>z1>(d1+d2)$, and the intermediate layer of a different Raman signature at depths z2 such that d1+d2<z2<d1. In the simulations reported herein the parameters d2 and d3 were fixed at 0.5 mm and 4 mm respectively, and d1 was varied from 0 to 3.5 mm to represent different depths of the interlayer 66 within the bulk of the sample 60.

The model assumed that all the illumination photons were first placed at a depth equal to the transport length lt and symmetrically distributed around the origin of the co-ordinate system x,y. The beam radius of the incident light r was 3 mm and the beam was given a uniform 'top-hat' intensity profile with all the photons having equal probability of being injected into the sample at any point within its cross-section. In the model, the Raman light was collected firstly at the top sample surface 62 from the illumination area of the incident light, and separately on the opposite side of the sample 64 symmetrically around the projection axis of the top collection/laser illumination area.

The laser beam photons were propagated through the medium by translating each individual photon in a random direction by a step t. At each step there was a given probability that the photon would be converted to a Raman photon. The absorption of photons was assumed to be insignificant in this simulation. This parameter is expressed as optical density for the conversion of laser beam photons to Raman light. That is, for example, an optical density (OD) of 1 or 2 per 1 mm corresponds to the 10-fold or 100-fold decrease of the number of illumination photons through conversion to Raman photons, respectively, passing through an overall propagation distance of 1 mm. The optical density accounting for the conversion of illumination photons into Raman photons was set to 0.01 per millimetre. Although this value is higher than that of real conversion, it only affects the absolute number of Raman photons, and not the spatial dependencies of concern in the studied regime. When an illumination photon is converted into a Raman photon the layer where this occurred is identified and recorded. Raman photons are propagated in the same fashion as illumination photons. A dominant mechanism for photon escape exists at the sample-to-air interfaces 62,64, as all the laser photons emerging from the sample at these interfaces do not return back into the sample and are effectively lost from the migration process. A Raman photon emerging at the top or bottom interface within the collection aperture of radius 3 mm centred on the axis of the laser beam are separately counted as detected Raman photons. Any photon emerging from the sample is eliminated from further calculations.

The numerical code for putting the model into effect was written in Mathematica 5.0 (Wolfram Research). 100,000 simulated photons were propagated, each over an overall distance of 40 mm which is in line with typical migration times observed in Raman spectroscopy in the absence of absorption. The step size used was t=0.2 mm (i.e. 200 steps was used). This corresponds to a sample formed from a powder having particle sizes of 10 and 20 µm diameter for the anisotropy of 0.9 and 0.95, respectively. Thus, the particle dimensions are comparable with that of most epithelial cells which are of the order of 10 to 20 µm in diameter. Moreover, many microcalcifications are also of this order. It was checked that upon these migration times the vast majority of photons were lost at sample-to-surface interfaces. This process was repeated 50-times. Hence the overall number of propagated photons was $10^6$ with the total number of steps considered being approximately $10^9$. All the detected Raman photons in these repeated runs were summed up.

Figure 5:
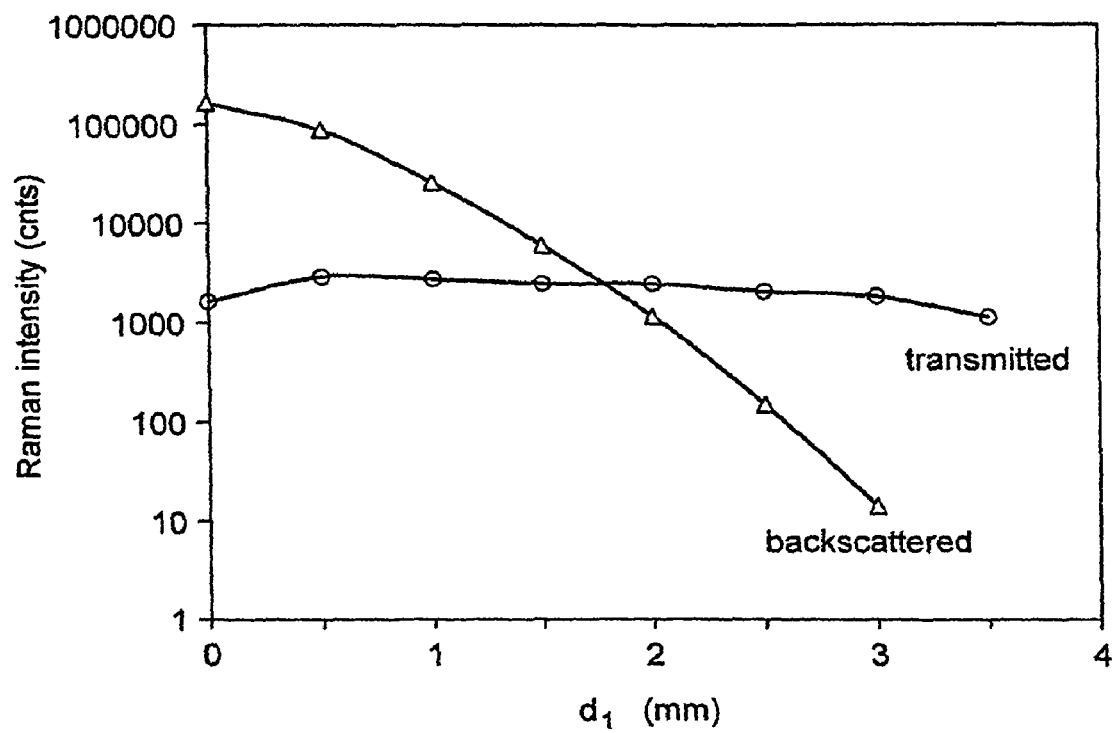
FIG. 5 shows graphs of Raman light intensity either backscattered through the illuminated surface, or forward scattered through an opposing surface, plotted according to the depth of the Raman scattering event, and calculated using the model of FIG. 4.

The number of Raman photons originating in the intermediate layer 66 and collected as backscattered photons at the upper surface 62, and transmitted photons at the lower surface 64, are shown in FIG. 5. The graphs show the number of backscattered and transmitted photons for eight different depths d1 of the intermediate layer 66 ranging from at the top surface where d1=0 mm to at the bottom surface where d1=3.5 mm.

From FIG. 5 it is clear that the collection of Raman photons in backscattering geometry even from an aperture as large as 6 mm in diameter leads to an extremely strong bias towards the surface layers of the sample body part. The repositioning of the 0.5 mm thick intermediate layer from the illuminated surface to a depth of 1.5 mm reduces the Raman backscatter intensity by 97%. In most practical applications the Raman signal will already have become swamped by the Raman or fluorescence signal originating from the surface region of the medium. At a depth of 3 mm the Raman signal originating from the intermediate layer has fallen by 4 orders of magnitude from its original level at the zero depth. On the other hand the dependence of the intensity of transmitted Raman photons exhibits only a weak dependence on the position of the intermediate layer within the sample. As the intermediate layer is moved between depths of 0 mm and 3.5 mm the corresponding Raman signal varies only by a factor of about 2. The absolute intensity of the Raman signal from the intermediate layer is only about 20-times lower than that of the bulk medium making detection relatively straightforward. Therefore the transmission geometry clearly provides a more representative sampling of the bulk of the body part interior than the conventional backscattering geometry, while permitting a satisfactory sensitivity.

For backscattering geometry, the model also reveals that an increase in sample body part thickness from 1 mm to 4 mm results in a 58% increase of the Raman signal detected in the backscattering geometry. In simplistic terms, this could be wrongly interpreted as extra Raman photons (amounting to 37% of the overall Raman signal observed for 4 mm thick body part) being produced in the extra 3 mm thickness added to the top 1 mm sample layer. However, the model of a 4 mm-thick body part indicates that 88% of Raman signal originates in the top 1 mm layer and only 12% originates within the remaining 3 mm of body part thickness. The extra 3 mm of material not only contributes with extra production of Raman photons but also reduces the loss of Raman photons originated within the 1 mm-layer at the lower surface 64. Thus the increase in backscattered Raman photons through the addition of a further 3 mm of sample is also accomplished by returning Raman photons originating near the upper surface back towards the upper surface from where they may emerge and be collected. In the same way, some illumination photons are scattered back towards the upper surface 62 allowing them to originate still more Raman photons within the top 1 mm layer.

Experimental Examples

Figure 6:
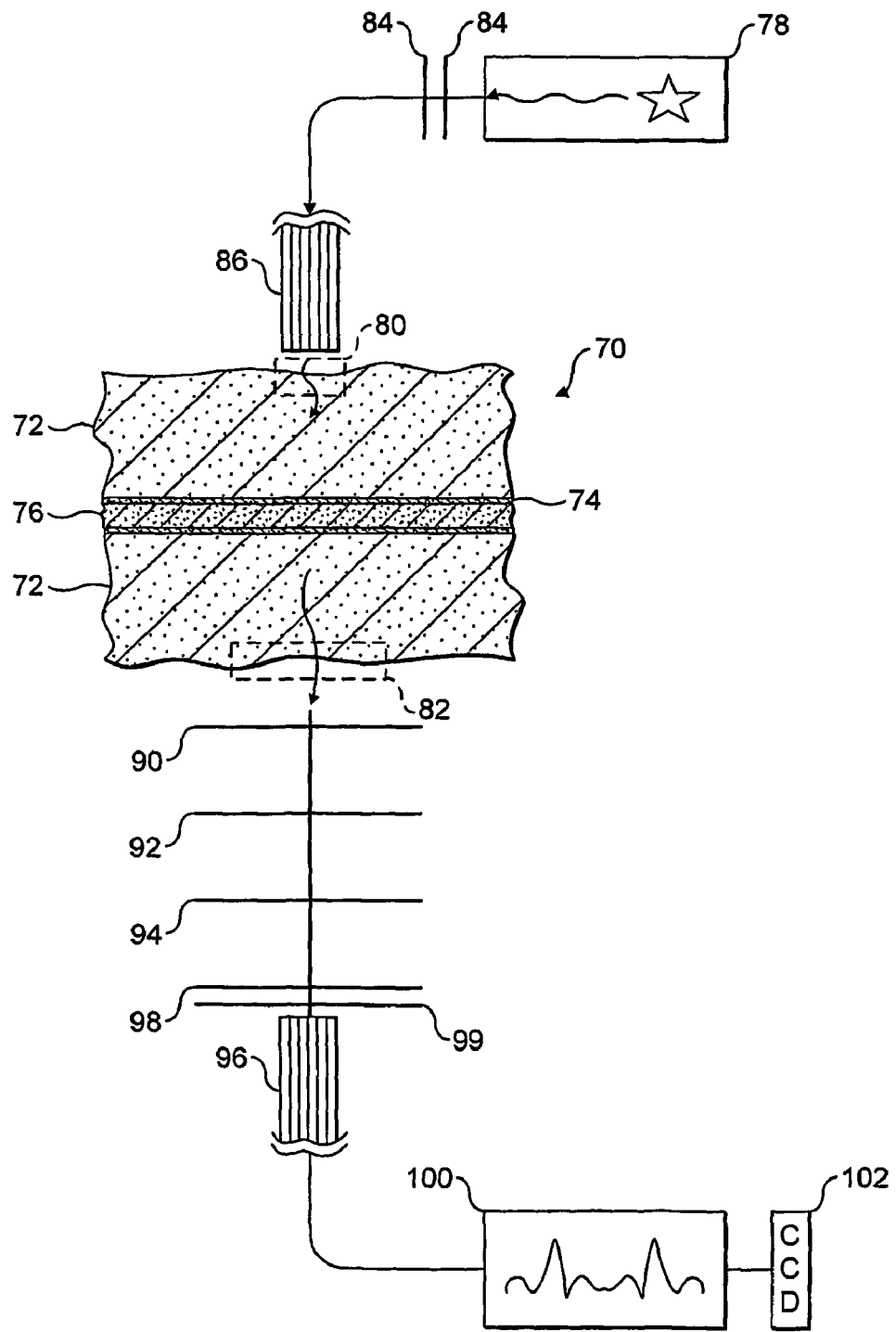
FIG. 6 illustrates an experimental arrangement demonstrating the principals of the invention on a sample of chicken breast enclosing an optical cell containing calcified material similar to that found in breast lesions.

The use of Raman spectroscopy in a transmission, forward scattering geometry was simulated in the laboratory as illustrated in FIG. 6. A sample 70 was constructed using raw chicken breast tissue 72 cut to about 8 mm thickness and wrapped around a transparent cell 74 having a 2 mm optical path length and lateral dimensions of 10 mm by 40 mm. Into the cell was place calcified material 76 for detection. The calcified material used was either calcium oxalate (dihydrate) (COD) or calcium hydroxyapatite (HAP), both of which are discussed above in the context of microcalcifications in breast tissue.

A laser 78 was used to generate an illumination beam directed at a first surface region 80 of the sample using illumination optics, and light scattered through the whole thickness of the sample including the optical cell 74 and two layers of chicken breast 72 to a second surface region 82 was gathered using collection optics. The Raman components of the collected light were then analysed to determine the degree to which the material in the optical cell could be detected and identified.

The illumination beam was generated using a temperature stabilised diode laser 78 suitable for Raman spectroscopy and operating at 827 nm (Micro Laser Systems, Inc, L4 830S-115-TE). The laser power at the first surface region was about 60 mW and the laser spot diameter at the first surface region was about 4 mm. The beam was spectrally purified by removing any residual amplified spontaneous emission components from its spectrum using two 830 nm Semrock® bandpass filters (84). These were slightly tilted to optimise throughput at the 827 nm laser wavelength.

The illumination optics were provided by a fibre optic probe 86 at which a bundle of seven core optical fibres and 26 outer ring fibres terminated. This probe was of the same construction as the probe used in the collection optics, described in more detail below.

The light scattered through the sample to the second surface region 82 was collected using the following collection optics. Light emerging from the region was gathered by a 50 mm diameter lens 90 with a focal length of 60 mm. The gathered light was collimated and passed through a 50 mm diameter holographic notch filter 92 (830 nm, Kaiser Optical Systems, Inc) to suppress the elastically scattered component of light corresponding to the original laser frequency. The filter was also slightly tilted to optimise the suppression for the 827 nm elastic scatter. A second lens 94, identical to the first, was then used to image, with magnification 1:1, the sample interaction zone onto the front face of a fibre probe 96. The laser incident spot at the first surface region was positioned in such a way so that it coincided with the centre of the probe axis as projected through the imaging system onto the sample. A 25 mm diameter holographic notch filter, 830 nm, Kaiser Optical Systems, Inc. (98) and an edge filter, 830 nm, Semrock (99) were used just before the probe 96 to suppress any residual elastically scattered light that passed through the first holographic filter 92.

The fibre probe 96 was comprised of 7 fibres placed tightly packed at the centre of the probe and 26 fibres distributed on a ring of 3 mm radius. The fibres were made of silica with a core diameter of 200 μm, cladding diameter of 230 μm and numerical aperture of 0.37. Sleeves were stripped on both ends for tighter packing of the fibres. The bundle was custom made by C Technologies Inc. The Raman light was propagated through the fibre systems of length ~1 m to the linear fibre end oriented vertically and placed in the input image plane of a Kaiser Optical Technologies Holospec f#=1.4 NIR spectrograph 100 with its slit removed. In this orientation the fibres themselves acted as the input slit of the spectrograph. The Raman spectra were collected using a deep depletion cooled CCD camera 102 by binning the signal from both sets of fibres into a single spectrum (full vertical chip binning). The Raman spectra are not corrected for the variation of detection system sensitivity across the active spectral range.

Figure 7A:
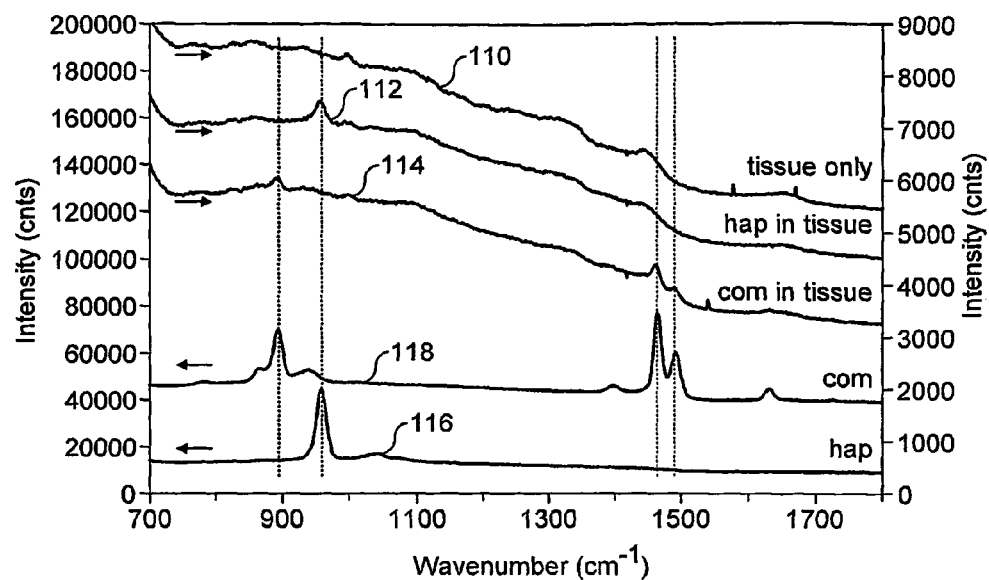
FIG. 7a shows spectra obtained with the cell empty, and containing either HAP or COM calcified material.

FIG. 7a shows spectra measured using the above arrangement when the optical cell was empty (110), when the optical cell was filled with HAP powder (112) and when the optical cell was filled with COM powder (114). These spectra are drawn with reference to the scale on the right hand axis, with additional arbitrary offsets to separate the spectra in the vertical direction. For reference, spectra taken using the same experimental set up but omitting the chicken breast tissue are shown for HAP powder (116) and COM powder (118). These reference spectra are drawn with reference to the scale on the left hand axis, again with additional vertical offsets to separate the spectra. The principal features of the pure HAP and COM spectra are clearly visible in the respective curves 112 and 114 of the full experiment.

Figure 7B:
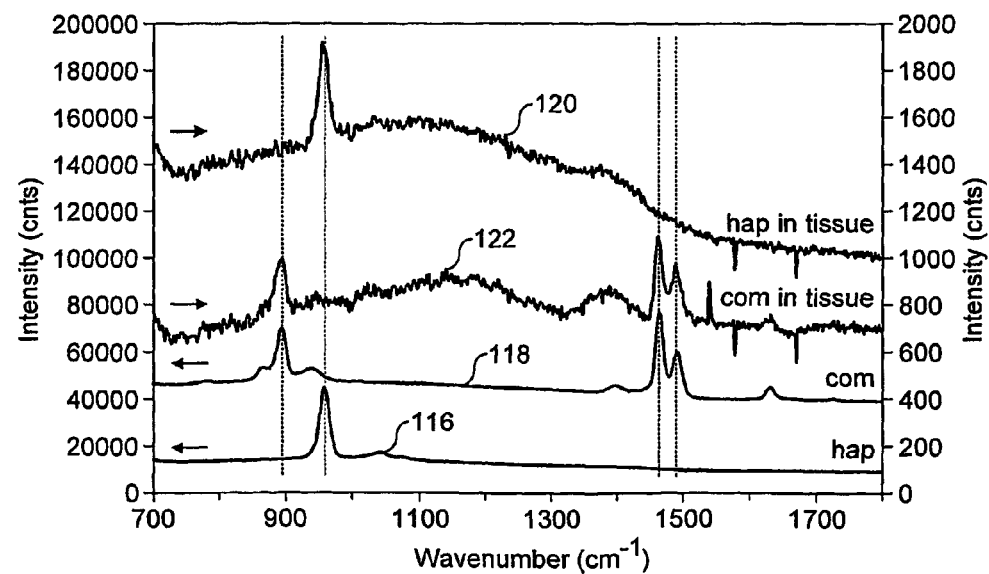
FIG. 7b shows the HAP and COM spectra of FIG. 7a with the empty cell background subtracted.

FIG. 7b is a presentation of the HAP (120) and COM (122) spectra of FIG. 7a with the tissue-only spectrum (110) subtracted therefrom, again with pure HAP and COM spectra shown for reference purposes.

Figure 7C:
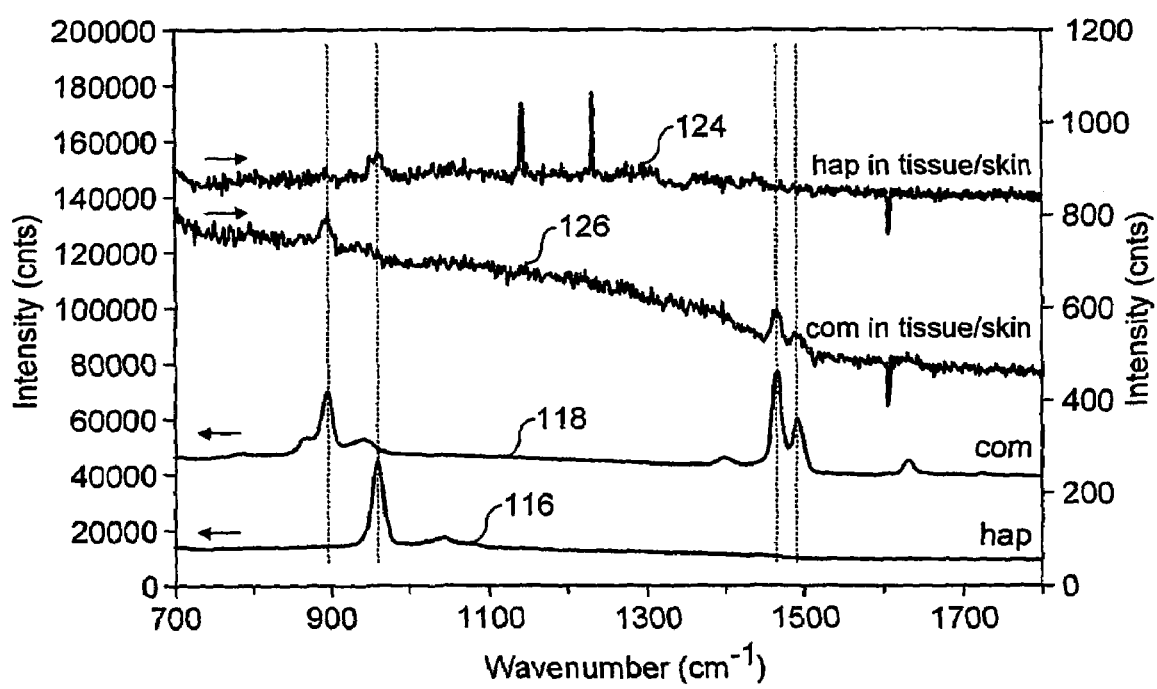
FIG. 7c shows spectra obtained in the same way as those of FIG. 7b but with chicken skin added to an outside surface of the sample.

The experiment was repeated with the addition of a layer of chicken skin to one surface of the sample, and FIG. 7c, which is otherwise the same as FIG. 7b, shows the results of this experiment with the background subtracted HAP spectrum as 124 and the background subtracted COM spectrum as 126.

In all cases shown in FIGS. 7a-7c the principal spectral characteristics of the HAP or COM material are clearly visible even though the collected light has been scattered through 16 mm or more of tissue.

Figure 8A:
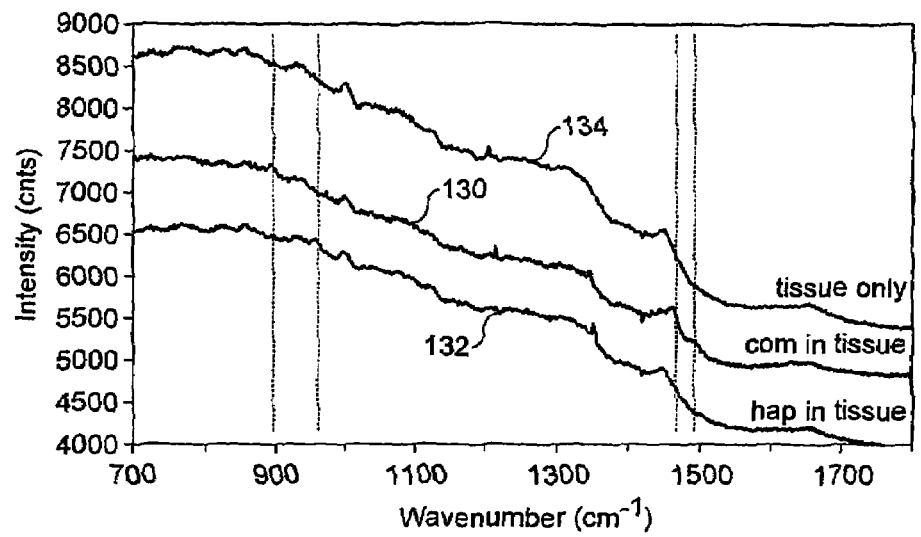
FIG. 8a shows spectra obtained by smearing the HAP or COM material onto an interior surface of the chicken breast in a thin layer instead of using an optical cell.
Figure 8B:
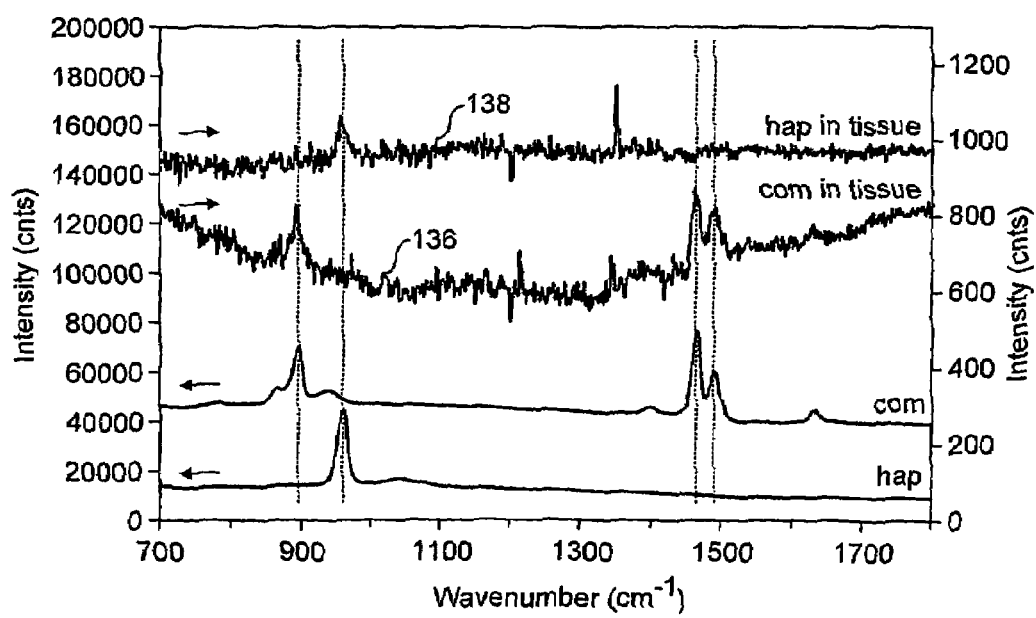
FIG. 8b shows the HAP and COM spectra of FIG. 8a with the tissue only background spectrum subtracted.

In some further experiments a sample was prepared without using an optical cell. Instead, either COM or HAP powder was smeared on chicken breast tissue so as to present a layer of calcified material about 100-300 μm thick, between two layers of chicken breast tissue each about 16 mm thick. FIG. 8a shows spectra taken using this sample using COM powder (130), HAP powder (132), and as a control background with no powder layer (134). The COM and HAP spectra with the background spectrum subtracted are shown in FIG. 8b as curves 136 and 138 respectively, with pure COM and Hap spectra shown for reference. Despite the small amount of COM and HAP material present in the samples, the principal spectral features identifying these substances are still clearly visible.

Although the experiments discussed above demonstrate adequate signal strength for clinical applications, the sensitivity and penetration depth of the technique can be improved further by increasing the power of the incident light beam and the efficiency of the collection system. For example, the incident light beam and consequently the first surface region may be enlarged, for example to a diameter of several centimetres, allowing incident light beam powers approaching 1 Watt to be used safely. The collection optics may be similarly scaled to collect as much of the transmitted light as possible, for example using imaging optics, a large fibre bundle, or both to cover an large second surface region.

The illumination and collection optics can take a variety of forms. The illumination light may be projected onto the first surface region from wide range of distances, depending on the detailed circumstances of the application, using imaging optics or optical fibres.

Although the invention has been principally described in relation to non invasive in vivo clinical applications, essentially the same methods and apparatus using Raman spectroscopy in a transmission geometry may be used to characterise in-vivo tissues during surgical or invasive procedures. Such procedures may be minimally invasive, for example by inserting just one of the illumination or collection optics within an opening, for example under the skin, using a needle probe or similar.

It will be apparent to the skilled person that various modifications and variations can be made to the described embodiments without departing from the spirit and scope of the invention.

The invention claimed is:

1. A method of probing a sample of living tissue including one or more calcifications, the method comprising:
    directing incident radiation at a first surface of the sample;
    discriminating between backscattered elements, and forward scattered and transmitted elements of said incident radiation by said sample, and collecting said forward scattered and transmitted elements of said incident radiation from a second surface of the sample, the second surface being spaced from said first surface such that at least a portion of said tissue lies directly between said first and second surfaces; and detecting Raman radiation arising from Raman scattering by said one or more calcifications in the collected radiation.

2. The method of claim 1 wherein said second surface is on an opposing side of the sample from the first surface, at least during the steps of directing and collecting.

3. The method of claim 1 wherein a measurement of composition of said one or more calcifications from said Raman radiation includes a measurement of at least one of a type 1, calcium oxalate material and a type calcium phosphate or calcium hydroxyapatite material.

4. The method of claim 1 further comprising compressing a breast which includes said living tissue between opposing clamp surfaces such that said first surface and said second surface of the breast are urged towards each other by the clamp surfaces.

5. A method of diagnosing a breast cancer condition comprising carrying out the method steps of claim 1 to determine a measurement of composition of said one or more calcifications and making a diagnosis of a breast cancer condition based on said measurement of composition.

6. The method of claim 1 wherein the tissue comprises at least one of bone, cartilage, bone marrow, brain, nerves, lipids, blood, teeth and breast tissue.

7. The method of claim 1 wherein the step of detecting is a step of detecting, in said collected radiation, characteristics of said radiation arising from Raman scattering by said one or more calcifications.

8. Apparatus for non invasive in-vivo measurement of composition of one or more calcifications comprised in a tissue within human or animal subject, the apparatus comprising:

illumination optics arranged to direct probe light at a first surface of the subject;

collection optics arranged so as to discriminate between backscattered light elements, and forward scattered and transmitted light elements by a portion of said tissue which receives said probe light, wherein said portion of said tissue lies between the first surface of the subject and a second surface of the subject, the second surface being spaced from said first surface such that said portion of said tissue lies directly between said first and second surfaces, and said collection optics being arranged to collect, from the second surface of the subject, said forward scattered and transmitted light elements by said portion of said tissue which lies between said first and second surfaces;

a light source arranged to provide said probe light to the illumination optics; and an analyser adapted to receive collected light from the collection optics and to determine one or more Raman spectral characteristics of the collected light, for said one or more calcifications.

9. The apparatus of claim 8 further comprising a data processor arranged to receive the determined one or more Raman spectral characteristics and to derive therefrom one or more indications of composition of the tissue.

10. The apparatus of claim 8 further comprising a restraint arranged to constrain movement of at least a part of the subject containing said tissue.

11. The apparatus of claim 8 further comprising an X-ray source and an X-ray detector arranged to determine characteristics of said tissue.

12. The apparatus of claim 8 further comprising a data processor adapted to determine a measurement of composition of said one or more calcifications comprised in the tissue from said characteristics.

13. The apparatus of claim 8 arranged such that the tissue is between the illumination optics and collection optics.

14. The apparatus of claim 13 wherein said illumination optics are arranged to direct radiation through a first surface of a breast, and said collection optics are arranged to collect a portion of said radiation emerging from the breast through a second surface of the breast.

15. The apparatus of claim 8 wherein the tissue comprises at least one of bone, cartilage, bone marrow, brain, nerves, lipids, blood, teeth and breast tissue.

16. The apparatus of claim 8 wherein the apparatus further comprises a data processor arranged to receive the determined one or more Raman spectral characteristics of the collected light and to derive therefrom one or more indications of composition of said one or more calcifications.

* * * * *